United States Patent [19]

Tsuchiya et al.

[11] Patent Number: 5,747,343
[45] Date of Patent: May 5, 1998

[54] LEUKOCYTE CLASSIFICATION REAGENT

[75] Inventors: Katsuhiro Tsuchiya; Yutaka Nagai; Mami Ikeda, all of Tokyo, Japan

[73] Assignee: Nihon Kohden Corporation, Tokyo, Japan

[21] Appl. No.: 550,861

[22] Filed: Oct. 31, 1995

[30] Foreign Application Priority Data

Oct. 31, 1994 [JP] Japan .................... 6-266573

[51] Int. Cl.$^6$ .................... G01N 33/48
[52] U.S. Cl. .................... 436/63; 436/10; 436/17; 436/18
[58] Field of Search .................... 436/10, 17, 18, 436/63

[56] References Cited

U.S. PATENT DOCUMENTS

| | | | |
|---|---|---|---|
| 4,528,274 | 7/1985 | Carter et al. | 436/10 |
| 4,637,986 | 1/1987 | Brown et al. | 436/10 |
| 5,116,539 | 5/1992 | Hamaguchi et al. | 252/408.1 |
| 5,128,265 | 7/1992 | Meiattini | 436/17 |
| 5,242,832 | 9/1993 | Sakata et al. | 436/17 |
| 5,250,437 | 10/1993 | Toda et al. | 436/10 |
| 5,264,369 | 11/1993 | Sakata et al. | 436/63 |
| 5,389,549 | 2/1995 | Hamaguchi et al. | 436/10 |
| 5,413,938 | 5/1995 | Tsujino et al. | 436/63 |
| 5,496,734 | 3/1996 | Sakata | 436/63 |
| 5,538,893 | 7/1996 | Sakata et al. | 436/10 |

FOREIGN PATENT DOCUMENTS

| | | |
|---|---|---|
| 0214613 | 3/1987 | European Pat. Off. . |
| 0316453A1 | 5/1988 | European Pat. Off. . |
| 0424871 | 5/1991 | European Pat. Off. . |

*Primary Examiner*—Jill Warden
*Assistant Examiner*—Sharidan Carrillo
*Attorney, Agent, or Firm*—Sughrue, Mion, Zinn, Macpeak & Seas, PLLC

[57] ABSTRACT

A leukocyte classification reagent comprising at least one surface active agent selected from the group consisting of anionic active agents and amphoteric active agents lyses erythrocytes within a short period of time when added to a blood sample but does not cause damage on leukocytes for a certain period of time keeping their original state or close to the original state so that leukocytes can be classified directly into four groups, namely lymphocyte, monocyte, neutrophil and eosinophil, by measuring forward scattering and side-way scattering by a flow cytometer after lysis of erythrocytes.

19 Claims, 5 Drawing Sheets

LEUKOCYTE CLASSIFICATION REAGENT

FIELD OF THE INVENTION

This invention relates to a reagent to be used in the field of clinical inspection for the classification of blood cells, more particularly to a reagent for use in a method for the classification of leukocytes in which blood cells after lysis of erythrocytes are optically measured using a flow cytometer.

BACKGROUND OF THE INVENTION

In a commonly used method for the classification and counting of leukocytes, an erythrocyte lysing agent (to be referred to as "hemolytic agent" hereinafter) mainly composed of a quaternary ammonium salt as a cationic surface active agent is added to a diluted blood solution to dissolve membranes and cytoplasmic contents of erythrocytes and leukocytes, and the remaining leukocyte nuclei are measured based on the Coulter's theory to count the number of leukocytes. Since leukocytes are observed in the shrunken form, this method has a problem in that information for the classification of leukocytes cannot be obtained.

In a method which has been developed with the aim of overcoming this problem by improving components of the hemolytic agent and their concentrations and slackening the reaction of leukocytes, leukocytes are classified into three groups, namely lymphocyte, monocyte and granulocyte, based on the difference in their lysing rate and electric conductivity. However, great concern has been directed in recent years toward the development of a method which can classify leukocytes into five groups including lymphocyte, monocyte, neutrophil, eosinophil and basophil, or at least four groups excluding basophil, because such a method can contribute to the diagnosis of diseases by counting blood leukocytes as individual groups.

Figure 10:
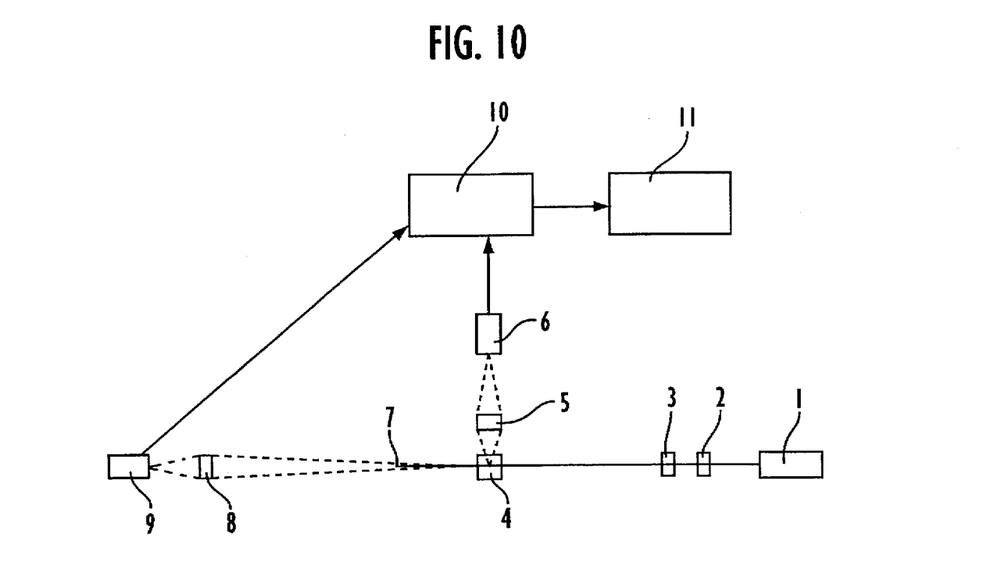
FIG. 10 is a schematic illustration showing the optical system of a flow cytometer in which the leukocyte classification reagent of the present invention is used.

On the other hand, a flow cytometer has been used for the identification and analysis of cells and fine particles based on light scattering. As shown in FIG. 10, a flow analyzer 4 of this cell measuring apparatus (flow cytometer) is designed to measure scattering from sample particles. That is, a sample solution containing particles to be measured is introduced into the flow analyzer 4 where laser beams generated from a laser source 1 are irradiated through radiation scattering lenses 2 and 3, the forward scattering after stoppage of direct light through an irradiation light stopper is measured by a forward scattering detector 9 via a forward scattering detection lens 8, and the voltage level measured by the detector is recorded in the analyzer 10. On the other hand, the side-way scattering in the flow analyzer 4 is measured by a side-way scattering detector 6 via a side-way scattering detection lens 5, and the voltage level measured by the detector is recorded in the analyzer 10. Based on both of the voltage levels in the analyzer 10, a two-dimensional distribution diagram (scattergram) of the forward scattering and side-way scattering is displayed on a display device 11.

However, such a measurement by a flow cytometer can count the number of leukocytes but it can hardly classify them even into three groups, because leukocyte membranes are lysed in significant quantity when the above-described hemolytic agent mainly composed of a quaternary ammonium salt surface active agent is used.

In a method in which leukocytes are classified by measuring forward scattering and side-way scattering making use of a flow cytometer, leukocytes are classified into three groups, namely lymphocyte, monocyte and granulocyte, by adding a hemolytic agent containing ammonium oxalate as its main component to a diluted blood solution to effect selective lysis of erythrocytes. This method, however, requires 20 to 30 minutes for the lysis of erythrocytes so that it cannot be used as a method for use in the treatment of a large number of samples. What is more, since distribution of each leukocyte group is not clear and eosinophil is included in the distribution of neutrophil, this method cannot isolate eosinophil as its single distribution.

For the purpose of overcoming the above-described problems, a leukocyte classification agent has been proposed (cf. WO 88/09504) which contains at least one surface active agent (hereinafter sometimes referred to as merely "active agent") selected from the group consisting of polyoxyethylene anionic active agents and polyoxyethylene nonionic active agents and which can classify leukocytes into 3 to 5 groups.

Both of these polyoxyethylene anionic and nonionic active agents are commonly represented the formula wherein $R_1$ represents an alkyl or alkenyl group having 10 to 22 carbon atoms, $R_2$ represents O, or COO, n is an integer of from 8 to 30 and A represents $SO_3Na$, COONa, $OSO_3Na$ or ONa in the case of the anionic active agent or H in the case of the nonionic active agent.

Thus, it has a relatively large ethylene oxide addition mol number of from 8 to 30. Such a large ethylene oxide addition mol number causes reduction of cytolytic activity. In addition, when a two-dimensional distribution diagram is obtained based on the results of measurements by RF and DC methods making use of this reagent, separation of lymphocyte, monocyte and granulocyte is poor and eosinophil cannot be measured at the same time.

SUMMARY OF THE INVENTION

In view of the above, an object of the present invention is to provide a leukocyte classification reagent (hemolytic agent) which lyses erythrocytes within a short period of time when added to a blood sample solution but does not cause damage on leukocytes for a certain period of time keeping their original state or close to the original state, so that leukocytes can be classified directly into four groups, namely lymphocyte, monocyte, eosinophil and neutrophil, by measuring forward scattering and side-way scattering by a flow cytometer after lysis of erythrocytes.

Accordingly, the present invention provides a leukocyte classification reagent which comprises at least one surface active agent selected from the group consisting of anionic active agents and amphoteric active agents in an amount effective to classify leukocytes in a blood sample by lysing erythrocytes and acting upon leukocytes. Specifically, the above anionic active agent is an alkyl sulfate anionic active agent represented by the formula (1):

(1)

wherein R represents an alkyl or alkylene group having 8 to 18 carbon atoms and X represents Na, K, $NH_4$ or $HN(CH_2CH_2OH)_3$; or a polyoxyethylene anionic active agent represented by the formula (2):

$$R-O-(CH_2CH_2O)_n-SO_3X \quad (2)$$

wherein R represents an alkyl or alkylene group having 8 to 18 carbon atoms, n is an integer of 1 to 5 and X represents Na, K, NH$_4$ or HN(CH$_2$CH$_2$OH)$_3$. More specifically, the polyoxyethylene anionic active agent is selected from the group consisting of sodium polyoxyethylene(3) C$_{12-13}$ alkyl ether sulfate, sodium polyoxyethylene(3) C$_{11-15}$ alkyl ether sulfate, polyoxyethylene(3) alkyl C$_{11-15}$ alkyl ether triethanolamine and sodium lauryl sulfate. The anionic active agent can also be a coconut fatty acid anionic active agent represented by the formula (3):

$$R-CONCH_2-X-Y \atop \quad\ \ | \atop \quad\ \ CH_3 \quad (3)$$

wherein R represents an alkyl or alkylene group having 8 to 18 carbon atoms, X represents CH$_2$SO$_3$ or COO and Y represents Na, K, NH$_4$ or HN(CH$_2$CH$_2$OH)$_3$. Specifically, the coconut fatty acid anionic active agent is sodium coconut fatty acid methyltaurine or sodium coconut fatty acid sarcosine.

The above-described amphoteric active agent is a 2-alkyl-N-carboxymethyl-N-hydroxyethyl imidazoliniumbetaine represented by the formula (4):

wherein R represents an alkyl or alkylene group having 6 to 21 carbon atoms. Specifically, the amphoteric active agent is 2-alkyl(C$_8$H$_{17}$–C$_{18}$H$_{37}$)-N-carboxymethyl-N-hydroxyethyl imidazoliniumbetaine.

BRIEF DESCRIPTION OF THE DRAWINGS

In the above drawings, 0 represents erythrocyte ghost, 1 represents lymphocyte, 2 represents monocyte, 3 represents neutrophil and 4 represents eosinophil.

DETAILED DESCRIPTION OF THE INVENTION

Any anionic and amphoteric surface active agent can be used in the leukocyte classification reagent of the present invention as long as it enables lysis of erythrocytes within a short period of time when they are added to a blood sample solution without causing damage on leukocytes to maintain the original state of leukocytes or close to the original state.

In the alkyl sulfate anionic active agent represented by the formula (1), the group R preferably has 8 to 18 carbon atoms. In the above-described polyoxyethylene anionic active agent represented by the formula (2), R preferably has 8 to 18 carbon atoms and ethylene oxide addition mol numbers of 1 to 5. Hydrogen in the alkyl or alkylene group R takes a great role in the lysis of cells. The longer the chain length of R is, the stronger the cytolytic activity is, while the shorter the chain length is, the weaker the cytolytic activity is. However, the water solubility of the surface active agent becomes lower as the chain length of R becomes longer and the agent is sparingly soluble or makes a hemolysate turbid. The number of carbon atoms in the group R within the above-described range balances these cases with each other. Also, as the integer represented by n becomes larger, hydrophilicity of the agent increases, but its cytolytic activity is reduced. The group X does not take particular role in the reaction upon blood cells.

The above description concerning the carbon number of R is also applicable to the coconut fatty acid anionic active agent represented by the formula (3), and thus it preferably has 8 to 18 carbon atoms. In the same manner as described above, both of the groups X and Y in the formula (3) do not take particular role in the reaction upon blood cells.

The amphoteric active agent acts as an anionic active agent or a cationic active agent depending on the pH range, and it acts as an anionic active agent when used as a hemolytic agent at a pH value of 7 or higher. In the betaine amphoteric active agent represented by the formula (4), R preferably has 6 to 21 carbon atoms.

According to the present invention, each blood sample is diluted with a usual diluent in order to effect uniform dispersion of blood, prior to the addition of a hemolytic agent as the leukocyte classification reagent. Such a diluent comprises an osmotic pressure adjusting agent, a buffer agent, a chelating agent and an antimicrobial agent dissolved in proper amounts in distilled water, with its typical composition shown below.

Diluent

| | |
|---|---|
| sodium chloride | 9.0 g |
| potassium dihydrogenphosphate | 0.91 g |
| disodium hydrogenphosphate | 9.55 g |
| EDTA 2Na | 0.3 g |
| sodium 1-hydroxypyridine-2-thionate | 0.25 g |
| distilled water | 1000 ml |

The osmotic pressure adjusting agent is used to adjust the osmotic pressure of blood sample solutions to such a level that blood cells can exist stably, namely 250 to 400 mOsm/kg $H_2O$. When the osmotic pressure is higher than this range, hemolytic activity becomes strong, particularly accelerating lysis of erythrocytes, and neutrophils shrink a little. On the other hand, when the osmotic pressure is lower than this range, hemolytic activity becomes weak and the amount of erythrocyte ghost (unlysed erythrocyte residue) becomes particularly large.

It is desirable that the buffer agent can maintain blood sample solutions within a pH range of approximately from 6.8 to 7.6 so that blood cells can exist stably. However, when a hemolytic agent is added to a blood sample solution, the pH value must be within the optimum range of the agent. In consequence, a pH value outside the above range is applicable with the proviso that it does not spoil the purpose of the present invention.

The purpose of the present invention can also be achieved by adding the hemolytic agent to the diluent in advance or by adding an appropriate amount of the surface active agent to the diluent directly without dilution.

The anionic active agent of the present invention acts as the hemolytic agent generally within the pH range of from 3 to 11, and the amphoteric active agent within the pH range of from 7 to 11, though the optimum range varies depending on their kinds. When the pH value is higher than these ranges, hemolytic activity becomes strong to cause lysis of not only erythrocytes but also leukocytes. On the other hand, when the pH value is lower than these ranges, hemolytic activity becomes weak so that separation of distributions of respective leukocyte components becomes poor.

The chelating agent is used to effect formation of chelate compounds with metal ions, in order to prevent generation of precipitate caused by metal ions during preservation of the diluent for a prolonged period of time or at the time of its use.

The antimicrobial agent is used to prevent growth of fungi and bacteria during long-term preservation of the diluent.

The amount of the hemolytic agent which contains the above-described surface active agent as the main component to be added to a blood sample diluted with the above-described diluent varies depending on the kind of the surface active agent. In general, however, the amount of ghost increases when the concentration of the surface active agent in the blood sample solution is so low that entire erythrocytes cannot be lysed. On the other hand, not only erythrocytes but also leukocytes are lysed when the active agent concentration is high. In addition, the time for hemolysis varies depending on the added amount of the hemolytic agent. The time for hemolysis becomes short when the added amount is large, but stable period of leukocytes also becomes short. In consequence, it is necessary to select proper amount of the surface active agent to be added. One of ordinarily skilled in the art can easily determine the appropriate concentration of the surface active agent. For example, 1 ml of a hemolytic agent prepared by dissolving the polyoxyethylene anionic active agent represented by the above-described formula (2) in distilled water to give a concentration of 0.05% can be added to a blood sample obtained by diluting 50 µl of whole blood with 2 ml of the above-described diluent. The amount of the hemolytic agent should be determined depending on a dilution ratio of blood and the concentration of the surface active agent.

Examples of the present invention are given below by way of illustration and not by way of limitation.

EXAMPLE 1

A polyoxyethylene anionic active agent, sodium polyoxyethylene(3) alkyl($C_{12-13}$ mixture) ether sulfate ($C_{12-13}$—O—$(CH_2CH_2O)_3$—$SO_3Na$), was used in this example as a hemolytic agent component.

A 1.75 g portion of this anionic active agent was dissolved in 1,000 ml of distilled water to serve as a hemolytic agent (if necessary, an appropriate amount of sodium chloride can be added to distilled water for the adjustment of osmotic pressure).

A 25 µl portion of a blood sample was diluted with 1 ml of a diluent having the following composition.

| | |
|---|---|
| sodium chloride | 9.0 g |
| potassium dihydrogenphosphate | 0.91 g |
| disodium hydrogenphosphate | 9.55 g |
| EDTA 2Na | 0.3 g |
| sodium 1-hydroxypyridine-2-thionate | 0.25 g |
| distilled water | 1000 ml |

Then, 125 µl of the above hemolytic agent was added thereto. Ten seconds thereafter, strengths of forward scattering and side-way scattering were measured using the flow cytometer to obtain a two-dimensional distribution diagram (scattergram) of FIG. 1.

Figure 1:
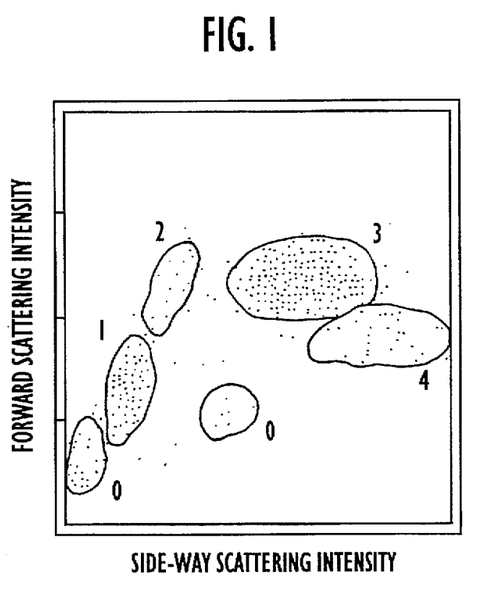
FIG. 1 is a two-dimensional distribution diagram when sodium polyoxyethylene(3) C$_{12-13}$ alkyl ether sulfate was used as a hemolytic agent.

As shown in FIG. 1, leukocytes were clearly classified into four groups, namely lymphocyte (1), monocyte (2), neutrophil (3) and eosinophil (4). In this drawing, (0) represents erythrocyte ghost.

In addition, two-dimensional distribution diagrams similar to the diagram shown in FIG. 1 were obtained when the above-described hemolytic agent (concentration, 0.175%) was added to the above-described diluted blood solution within the range of from 100 to 1,000 µl. In this instance, the purpose of the present invention can also be achieved by adding the hemolytic agent to the diluent in advance or by adding an appropriate amount of the above-described surface active agent to the diluent directly without dilution.

The surface active agent of this example showed the same result shown in FIG. 1 within the pH range of from 3 to 10.

With regard to the osmotic pressure, the same result shown in FIG. 1 was also obtained within the range of from 250 to 400 mOsm/kg $H_2O$.

EXAMPLE 2

Figure 2:
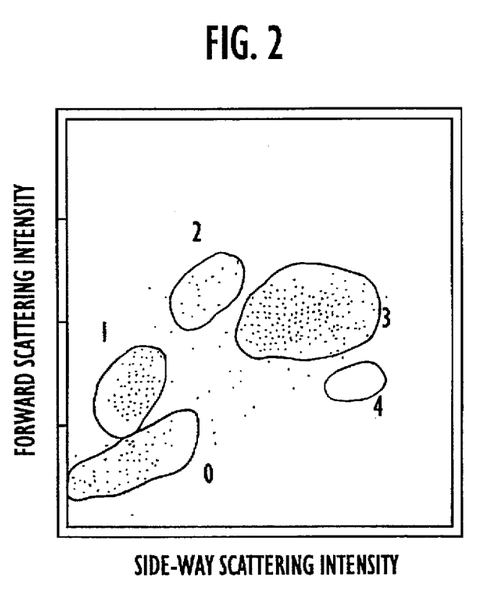
FIG. 2 is a two-dimensional distribution diagram when sodium polyoxyethylene(3) C$_{11-15}$ alkyl ether sulfate was used as a hemolytic agent.

Classification of leukocytes was carried out in the same manner as described in Example 1, except that a polyoxyethylene anionic active agent, sodium polyoxyethylene(3) alkyl($C_{11-15}$ mixture) ether sulfate, was used as a hemolytic agent component and 2.5 g of this anionic active agent was dissolved in 1,000 ml of distilled water to be used as a hemolytic agent, with the results shown in FIG. 2. As the result, leukocytes were clearly classified into four groups similar to the case of Example 1. Also, the same results shown in FIG. 2 were obtained within the addition range of from 50 to 300 µl (in the case of 0.25% hemolytic agent), within the pH range of from 6 to 10 and within the osmotic pressure range of from 250 to 400 mOsm/kg $H_2O$ similar to the case of Example 1.

EXAMPLE 3

Figure 3:
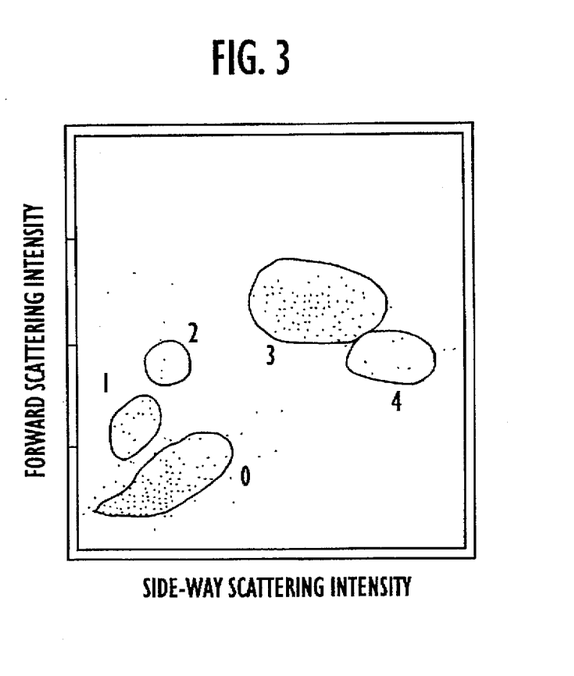
FIG. 3 is a two-dimensional distribution diagram when sodium lauryl sulfate was used as a hemolytic agent.

Classification of leukocytes was carried out in the same manner as described in Example 1, except that a polyoxyethylene anionic active agent, sodium lauryl sulfate ($C_{12}H_{25}OSO_3Na$), was used as the active ingredient of hemolytic agent and 5.0 g of this anionic active agent was dissolved in 1,000 ml of distilled water to be used as a hemolytic agent, with the results shown in FIG. 3. As the result, leukocytes were clearly classified into four groups similar to the case of Example 1. Also, in the case of 0.5% hemolytic agent, the same results shown in FIG. 3 were obtained within the addition range of from 50 to 200 μl, within the pH range of from 5 to 8 and within the osmotic pressure range of from 250 to 400 mOsm/kg $H_2O$ similar to the case of Example 1.

EXAMPLE 4

Using two types of the polyoxyethylene anionic active agent represented by the above-described formula (2) in which R has 8 and 18 carbon atoms and n is 3 in both types, leukocyte classification tests were carried out in the same manner as described in Examples 1 to 3. In both cases, scattergrams similar to those shown in FIGS. 1 to 3 were obtained in which leukocytes were clearly classified into four groups, namely lymphocyte, monocyte, neutrophil and eosinophil.

Comparative Example 1

Figure 4:
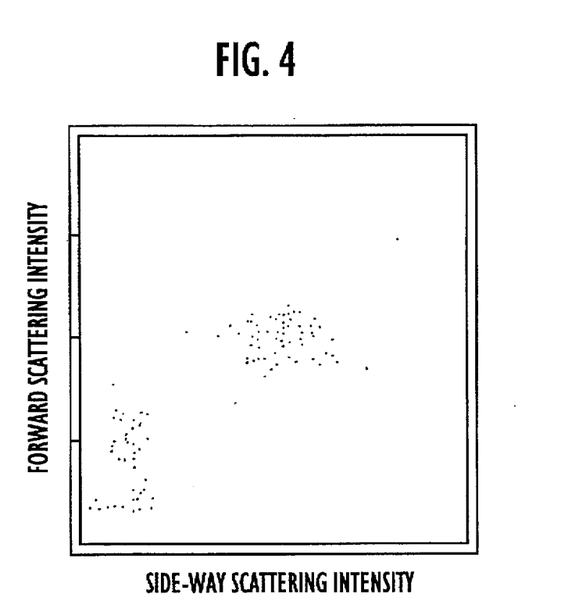
FIG. 4 is a two-dimensional distribution diagram when sodium lauryl sulfate was used as a hemolytic agent and classification of leukocytes was carried out at pH 10.
Figure 5:
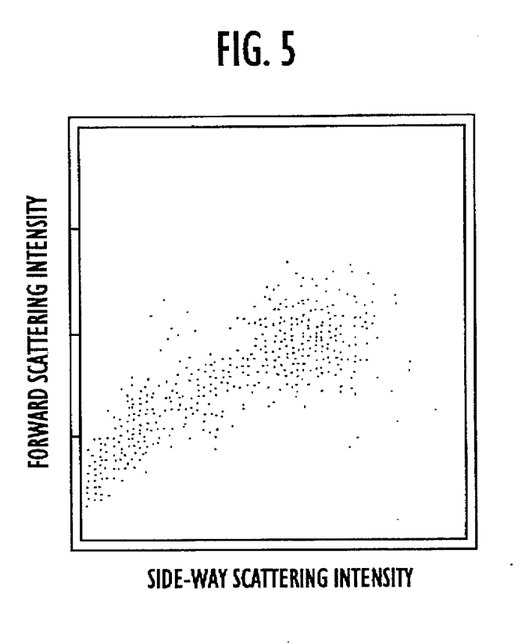
FIG. 5 is a two-dimensional distribution diagram when sodium lauryl sulfate was used as a hemolytic agent and classification of leukocytes was carried out at pH 3.

Using sodium lauryl sulfate as the active ingredient of hemolytic agent similar to the case of Example 3, effects of pH values 10 and 3 on the classification of leukocytes were examined. The results are shown in FIGS. 4 and 5, respectively. As is evident from the results shown in FIG. 4, only a hardly measurable two-dimensional distribution diagram is obtained at pH 10, because the hemolytic activity becomes too strong so that leukocytes and erythrocytes are lysed at the same time. On the other hand, as shown in FIG. 5, the hemolytic activity became too weak at pH 3 so that satisfactory results were not obtained due to poor separation of leukocytes.

Comparative Example 2

Figure 6:
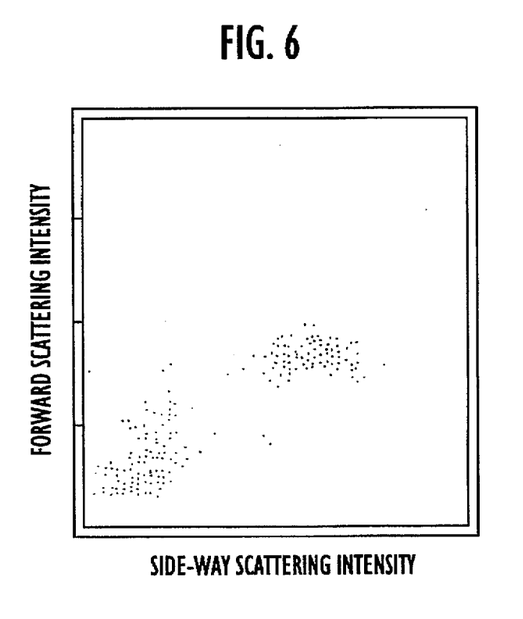
FIG. 6 is a two-dimensional distribution diagram when sodium polyoxyethylene(3) C$_{11-15}$ alkyl ether sulfate was used as a hemolytic agent and classification of leukocytes was carried out under an osmotic pressure of 450 mOsm/kg H$_2$O.
Figure 7:
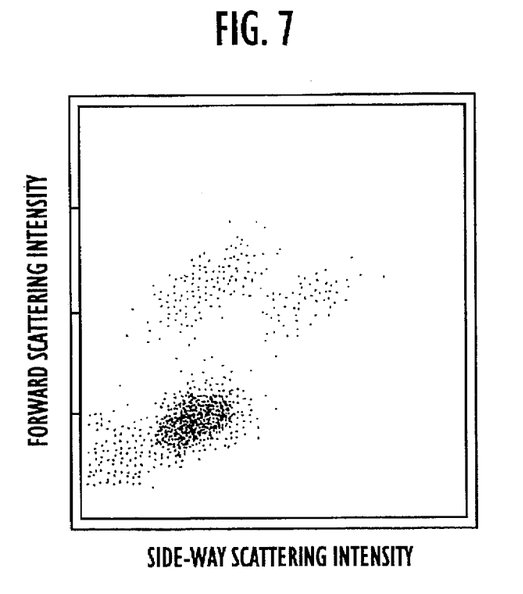
FIG. 7 is a two-dimensional distribution diagram when sodium polyoxyethylene(3) C$_{11-15}$ alkyl ether sulfate was used as a hemolytic agent and classification of leukocytes was carried out under an osmotic pressure of 220 mOsm/kg H$_2$O.

Using sodium polyoxyethylene(3) alkyl($C_{11-15}$ mixture) ether sulfate as the active ingredient of hemolytic agent similar to the case of Example 2, effects of the osmotic pressures of 450 and 220 mOsm/kg $H_2O$ on the classification of leukocytes were examined. At an osmotic pressures of 450 mOsm/kg $H_2O$, the hemolytic activity became so strong that lysis of erythrocytes progressed especially rapidly but lysis of leukocytes also progressed and neutrophils shrank a little, so that only a hardly measurable two-dimensional distribution diagram was obtained as shown in FIG. 6 similar to the case of high pH value shown in FIG. 4. At an osmotic pressures of 220 mOsm/kg $H_2O$, on the other hand, the hemolytic activity became so weak that the amount of erythrocyte ghost became particularly large and the results therefore were not satisfactory as shown in FIG. 7.

The same results were obtained when the alkyl group R and the ethylene oxide mol number n are outside the ranges defined in the foregoing.

EXAMPLE 5

A coconut fatty acid anionic active agent, sodium coconut fatty acid methyltaurine (R-CON($CH_3$)$CH_2CH_2SO_3Na$), was used as the active ingredient of hemolytic agent.

A 5.8 g portion of this anionic active agent was dissolved in 1,000 ml of distilled water to serve as a hemolytic agent (if necessary, an appropriate amount of sodium chloride can be added to distilled water for the adjustment of osmotic pressure similar to the case of Example 1).

Figure 8:
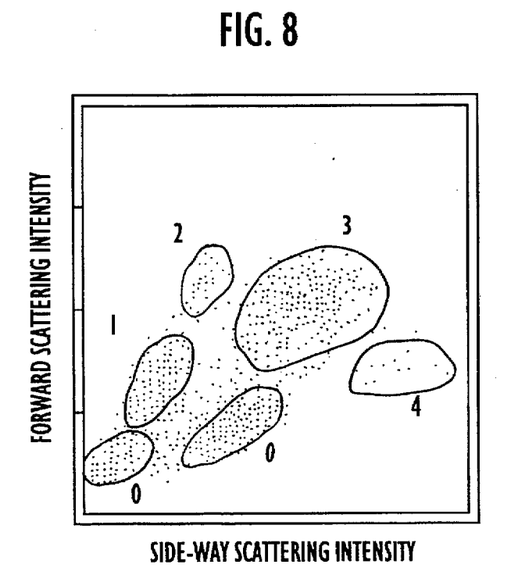
FIG. 8 is a two-dimensional distribution diagram when sodium coconut fatty acid methyltaurine was used as a hemolytic agent.

By repeating the procedure of Example 1, a two-dimensional distribution diagram shown in FIG. 8 was obtained.

As the result, leukocytes were clearly classified into four groups, namely lymphocyte (1), monocyte (2), neutrophil (3) and eosinophil (4). In this drawing, (0) represents erythrocyte ghost.

Figure 9:
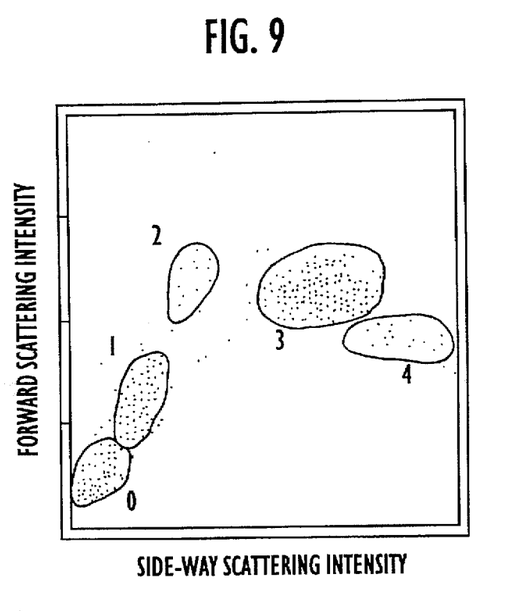
FIG. 9 is a two-dimensional distribution diagram when 2-C$_{8-18}$alkyl-N-carboxymethyl-N-hydroxyethyl imidazoliniumbetaine was used as a hemolytic agent.

Similar to the case of Example 1, when the active agent was used in a concentration of 0.58%, the same results shown in FIG. 9 were obtained within the addition range of from 50 to 300 μl, within the pH range of from 6 to 9 and within the osmotic pressure range of from 250 to 400 mOsm/kg $H_2O$.

EXAMPLE 6

A betaine amphoteric active agent, 2-alkyl ($C_8H_{17}$–$C_{18}H_{37}$ mixture)-N-carboxymethyl-N-hydroxyethyl imidazoliniumbetaine represented by the formula:

was used as the active ingredient of hemolytic agent.

A 3.6 g portion of this amphoteric active agent was dissolved in 1,000 ml of distilled water to serve as a hemolytic agent.

By repeating the procedure of Example 5, a two-dimensional distribution diagram shown in FIG. 9 was obtained.

As the result, leukocytes were clearly classified into four groups similar to the case of Examples 1 to 5.

Also similar to the case of Example 5, when the active agent was used in a concentration of 0.36%, the same results shown in FIG. 9 were obtained within the addition range of from 75 to 200 μl, within the pH range of from 7 to 11 and within the osmotic pressure range of from 250 to 400 mOsm/kg $H_2O$.

EXAMPLE 7

Using two types of the betaine amphoteric active agent represented by the above-described formula (3) in which R has 6 or 21 carbon atoms, leukocyte classification tests were carried out in the same manner as described in Example 6. In both cases, two-dimensional distribution diagrams similar to those shown in FIG. 9 were obtained in which leukocytes were clearly classified into four groups, namely lymphocyte, monocyte, neutrophil and eosinophil.

Thus, according to the present invention, the inventive leukocyte classification reagent can lyse erythrocytes within a short period of time when added to a diluted blood solution but does not cause damage on leukocytes, so that the original state of leukocytes or a state close thereto can be maintained for a certain period of time, and leukocytes therefore can be classified directly into four groups by simple procedure and construction, thus exerting great effects in the field of clinical inspection.

While the invention has been described in detail and with reference to specific examples thereof, it will be apparent to one skilled in the art that various changes and modifications can be made therein without departing from the spirit and scope thereof.

What is claimed is:

1. A leukocyte classification reagent which consists essentially of at least one surface active agent selected from the group consisting of an anionic active agent and an amphoteric active agent in an amount effective to classify leukocytes by lysing erythrocytes and acting upon leukocytes, wherein said anionic active agent is an alkyl sulfate anionic active agent represented by the formula (1):

$$R—O—SO_3X \qquad (1)$$

wherein R represents an alkyl or alkylene group having 8 to 18 carbon atoms and X represents Na, K, $NH_4$ or $HN(CH_2CH_2OH)_3$.

2. The reagent according to claim 1, wherein said alkyl sulfate anionic active agent is sodium lauryl sulfate.

3. A leukocyte classification reagent which comprises at least one surface active agent selected from the group consisting of an anionic active agent and an amphoteric active agents in an amount effective to classify leukocytes by lysing erythrocytes and acting upon leukocytes, wherein said anionic active agent is a polyoxyethylene anionic active agent represented by the formula (2):

$$R—O—(CH_2CH_2O)_n—SO_3—X \qquad (2)$$

wherein R represents an alkyl or alkylene group having 8 to 18 carbon atoms, n is an integer of 1 to 5 and X represents Na, K, $NH_4$ or $HN(CH_2CH_2OH)_3$.

4. The reagent according to claim 3, wherein said anionic active agent is selected from the group consisting of sodium polyoxyethylene (3) $C_{12-13}$ alkyl ether sulfate, sodium polyoxyethylene (3) $C_{11-15}$ alkyl ether sulfate, and polyoxyethylene (3) $C_{11-15}$ alkyl ether triethanolamine sulfate.

5. A leukocyte classification reagent which consists essentially of at least one surface active agent selected from the group consisting of an anionic active agent and an amphoteric active agent in an amount effective to classify leukocytes by lysing erythrocytes and acting upon leukocytes, wherein said anionic active agent is a coconut fatty acid anionic active agent represented by the formula (3):

$$R—CONCH_2—X—Y \atop | \atop CH_3 \qquad (3)$$

wherein R represents an alkyl or alkylene group having 8 to 18 carbon atoms, X represents $CH_2SO_3$ or $COO$ and Y represents Na, K, $NH_4$ or $HN(CH_2CH_2OH)_3$.

6. The reagent according to claim 5 wherein said coconut fatty acid anionic active agent is sodium coconut fatty acid methyltaurine or sodium coconut fatty acid sarcosine.

7. A leukocyte classification reagent which comprises at least one surface active agent selected from the group consisting of an anionic active agent and an amphoteric active agents in an amount effective to classify leukocytes by lysing erythrocytes and acting upon leukocytes, wherein said amphoteric active agent is a 2-alkyl-N-carboxymethyl-N-hydroxyethyl imidazoliniumbetaine represented by the formula (4):

wherein R represents an alkyl or alkylene group having 6 to 21 carbon atoms.

8. A leukocyte classification reagent which comprises at least one surface active agent selected from the group consisting of an anionic active agent and an amphoteric active agents in an amount effective to classify leukocytes by lysing erythrocytes and acting upon leukocytes, wherein said amphoteric active agent is 2-alkyl $(C_8H_{17}–C_{18}H_{37})$-N-carboxymethyl-N-hydroxyethyl imidazoliniumbetaine.

9. A process for classifying of leukocytes which comprises the steps of:

(A) adding a leukocyte classification reagent to a blood sample solution to lyse erythrocytes present in said blood sample solution and producing a hemolysate; and (B) subjecting the hemolysate of step (A) to flow cytometry to measure forward optical scattering and side-way optical scattering thereby producing a distribution diagram which classifies the leukocytes into a plurality of groups, wherein said reagent consists essentially of at least one surface active agent selected from the group consisting of an alkyl sulfate anionic active agent and an amphoteric active agent in an amount effective to classify leukocytes by lysing erythrocytes and acting upon leukocytes, wherein said alkyl sulfate anion active agent is represented by the formula (1):

$$R—O—SO_3X \qquad (1)$$

wherein R represents an alkyl or alkylene group having 8 to 18 carbon atoms and X represents Na, K, $NH_4$ or $HN(CH_2CH_2OH)_3$.

10. The process according to claim 9, wherein said alkyl sulfate anionic active agent is sodium lauryl sulfate.

11. A process for classifying of leukocytes which comprises the steps of:

(A) adding a leukocyte classification reagent to a blood sample solution to lyse erythrocytes present in said blood sample solution and producing a hemolysate; and (B) subjecting the hemolysate of step (A) to flow cytometry to measure forward optical scattering and side-way optical scattering thereby producing a distribution diagram which classifies the leukocytes into a plurality of groups, wherein said reagent consists essentially of at least one surface active agent selected from the group consisting of a coconut fatty acid anionic active agent and an amphoteric active agent in an amount effective to classify leukocytes by lysing erythrocytes and acting upon leukocytes, wherein said coconut fatty acid anionic active agent is represented by the formula (3):

$$R—CONCH_2—X—Y \atop | \atop CH_3 \qquad (3)$$

wherein R represents an alkyl or alkylene group having 8 to 18 carbon atoms, X represents $CH_2SO_3$ or $COO$ and Y represents Na, K, $NH_4$ or $HN(CH_2CH_2OH)_3$.

12. The process according to claim 11, wherein said coconut fatty acid anionic active agent is sodium coconut fatty acid methyltaurine or sodium coconut fatty acid sarcosine.

13. The reagent according to claims 4, 3, 7 or 8, wherein said reagent has a pH value ranging from 3 to 11.

14. The reagent according to claims 4, 3, 7 or 8, wherein said reagent has an osmotic pressure of from 250 to 400 $mOsm/kgH_2O$.

15. A process for classifying of leukocytes which comprises:

(A) adding the leukocyte classification reagent of claims 4, 3, 7 or 8, to a blood sample solution to lyse erythrocytes present in said blood sample solution and producing a hemolysate; and (B) subjecting the hemolysate of step (A) to flow cytometry to measure forward scattering and side-way scattering thereby producing a distribution diagram which classifies the leukocytes into a plurality of groups.

16. The reagent according to claim 1, 6, 2 or 5, wherein said reagent has a pH value ranging from 3 to 11.

17. The reagent according to claim 1, 6, 2 or 5, wherein said reagent has an osmotic pressure of from 250 to 400 mOsm/kgH$_2$O.

18. The process according to claim 9, 10, 11 or 12, wherein said reagent has a pH value ranging from 3 to 11.

19. The process according to claim 9, 10, 11 or 12, wherein said reagent has an osmotic pressure of from 250 to 400 mOsm/kgH$_2$O.

* * * * *